(12) United States Patent
Pierro et al.

(10) Patent No.: US 10,143,813 B2
(45) Date of Patent: *Dec. 4, 2018

(54) NASAL CONTINUOUS POSITIVE AIRWAY PRESSURE DEVICE

(71) Applicant: VYAIRE MEDICAL CONSUMABLES LLC, Yorba Linda, CA (US)

(72) Inventors: Brian Pierro, Yorba Linda, CA (US); Steven M. Harrington, Cardiff by the Sea, CA (US); Bruce K. Bridges, Cardiff by the Sea, CA (US); Douglas Gaylord, San Diego, CA (US)

(73) Assignee: Vyaire Medical Consumables LLC, Yorba Linda, CA (US)

( * ) Notice: Subject to any disclaimer, the term of this patent is extended or adjusted under 35 U.S.C. 154(b) by 281 days.

This patent is subject to a terminal disclaimer.

(21) Appl. No.: 14/923,238

(22) Filed: Oct. 26, 2015

(65) Prior Publication Data

US 2016/0045692 A1 Feb. 18, 2016

Related U.S. Application Data

(63) Continuation of application No. 13/967,222, filed on Aug. 14, 2013, now Pat. No. 9,168,346, which is a
(Continued)

(51) Int. Cl.
*A61M 16/08* (2006.01)
*A61M 16/06* (2006.01)
*A61M 16/00* (2006.01)

(52) U.S. Cl.
CPC .... *A61M 16/0057* (2013.01); *A61M 16/0666* (2013.01); *A61M 16/0825* (2014.02);
(Continued)

(58) Field of Classification Search
CPC ....... A61G 10/00; A61M 11/00; A61M 15/00; A61M 15/08; A61M 16/00;
(Continued)

(56) References Cited

U.S. PATENT DOCUMENTS

| 4,248,218 A | 2/1981 | Fischer |
| 4,262,665 A | 4/1981 | Roalstad et al. |

(Continued)

FOREIGN PATENT DOCUMENTS

| GB | 2170110 A | 7/1986 |
| JP | H1110371 | 4/1989 |

(Continued)

OTHER PUBLICATIONS

Extended European Search Report for Application No. 16180722.7, dated Mar. 2, 2017, 8 pages.

(Continued)

*Primary Examiner* — Annette Dixon
(74) *Attorney, Agent, or Firm* — Morgan, Lewis & Bockius LLP

(57) ABSTRACT

A nasal continuous positive airway pressure (nCPAP) device having a hollow body with a proximal wall, a distal wall, and an exhaust port extending through the distal wall. A proximal tubular member extends through the proximal wall of the body and is arranged such that a stream of gas entering the body through the proximal tubular member will exit the proximal tubular member in a first direction and then enter the exhaust port. A nozzle extends through the body and is arranged such that a stream of gas entering the body through the nozzle will exit the nozzle and then enter the proximal tubular member in a second direction that is opposite the first direction.

20 Claims, 17 Drawing Sheets

Related U.S. Application Data continuation of application No. 12/547,140, filed on Aug. 25, 2009, now Pat. No. 8,534,286, which is a continuation of application No. 11/293,883, filed on Dec. 2, 2005, now Pat. No. 7,578,294.

(52) U.S. Cl.
CPC ..... *A61M 16/0858* (2014.02); *A61M 16/0683* (2013.01); *A61M 2206/16* (2013.01)

(58) Field of Classification Search
CPC .............. A61M 16/0057; A61M 16/06; A61M 16/0616; A61M 16/0633; A61M 16/0666; A61M 16/0677; A61M 16/0683; A61M 16/08; A61M 16/0825; A61M 16/0833; A61M 16/10; A61M 16/12; A61M 16/127; A61M 16/20; A62B 17/00; A62B 18/00; A62B 18/02; A62B 18/10; A62B 7/00; A62B 18/08
USPC ............ 128/200.24, 200.26, 200.29, 203.12, 128/203.22, 204.11, 204.12, 204.18, 128/204.23, 204.24, 204.25, 205.27, 128/206.11, 206.12, 206.18, 206.21, 128/206.24, 206.26, 207.12, 207.13, 128/207.15, 207.18, 911, 912
See application file for complete search history.

(56) References Cited

U.S. PATENT DOCUMENTS

| | | | |
|---|---|---|---|
| 4,274,406 A | 6/1981 | Bartholomew | |
| 4,681,000 A | 7/1987 | Wolters | |
| 4,681,100 A * | 7/1987 | Brychta ............ | A61M 16/0833 128/204.25 |
| 4,782,832 A | 11/1988 | Trimble et al. | |
| 4,821,736 A | 4/1989 | Watson | |
| 4,915,105 A | 4/1990 | Lee | |
| 5,036,847 A | 8/1991 | Boussignac et al. | |
| 5,046,491 A | 9/1991 | Derrick | |
| 5,113,857 A | 5/1992 | Dickerman et al. | |
| 5,193,532 A | 3/1993 | Moa et al. | |
| 5,231,979 A | 8/1993 | Rose et al. | |
| 5,451,190 A | 9/1995 | Liardet | |
| 5,477,852 A | 12/1995 | Landis et al. | |
| 5,687,715 A | 11/1997 | Landis et al. | |
| 5,806,516 A | 9/1998 | Beattie | |
| 5,975,077 A | 11/1999 | Hofstetter et al. | |
| 6,119,694 A | 9/2000 | Correa et al. | |
| 6,158,434 A | 12/2000 | Lugtigheid et al. | |
| 6,273,087 B1 | 8/2001 | Boussignac et al. | |
| 6,478,026 B1 | 11/2002 | Wood | |
| 6,595,215 B2 | 7/2003 | Wood | |
| 6,769,432 B1 | 8/2004 | Keifer | |
| 6,772,754 B1 * | 8/2004 | Mendenhall ...... | A61M 15/0091 128/200.14 |
| 6,863,069 B2 | 3/2005 | Wood | |
| 6,997,187 B2 | 2/2006 | Wood et al. | |
| 7,000,613 B2 | 2/2006 | Wood et al. | |
| 7,080,645 B2 * | 7/2006 | Genger ................ | A61M 16/00 128/204.18 |
| 7,152,604 B2 | 12/2006 | Hickle et al. | |
| 7,156,096 B2 | 1/2007 | Landis | |
| 7,191,781 B2 | 3/2007 | Wood | |
| 7,219,669 B1 | 5/2007 | Lovell et al. | |
| 7,353,826 B2 | 4/2008 | Sleeper et al. | |
| 7,578,294 B2 * | 8/2009 | Pierro ............... | A61M 16/0666 128/204.18 |
| 7,762,258 B2 | 7/2010 | Zollinger et al. | |
| 8,100,125 B2 | 1/2012 | Duquette et al. | |
| 8,534,286 B2 * | 9/2013 | Pierro ............... | A61M 16/0666 128/200.24 |
| 9,168,346 B2 * | 10/2015 | Pierro ............... | A61M 16/0666 |
| 2002/0053347 A1 | 5/2002 | Ziaee | |
| 2003/0000527 A1 | 1/2003 | Stenzler et al. | |
| 2003/0079749 A1 | 5/2003 | Strickland et al. | |
| 2003/0200970 A1 * | 10/2003 | Stenzler ............ | A61M 16/0666 128/207.18 |
| 2004/0065330 A1 | 4/2004 | Landis | |
| 2004/0244804 A1 | 12/2004 | Olsen et al. | |
| 2005/0011524 A1 | 1/2005 | Thomlinson et al. | |
| 2005/0133039 A1 | 6/2005 | Wood | |
| 2005/0150493 A1 | 7/2005 | Foster et al. | |
| 2005/0199242 A1 | 9/2005 | Matula et al. | |
| 2005/0229928 A1 * | 10/2005 | Ivri ...................... | A61M 11/005 128/203.12 |
| 2005/0241644 A1 | 11/2005 | Gunaratnam et al. | |
| 2006/0042631 A1 | 3/2006 | Martin et al. | |
| 2006/0042634 A1 | 3/2006 | Nalagatla et al. | |
| 2006/0047185 A1 | 3/2006 | Shener et al. | |
| 2006/0130840 A1 | 6/2006 | Porat et al. | |
| 2006/0174887 A1 | 8/2006 | Chandran et al. | |
| 2006/0231103 A1 | 10/2006 | Matula et al. | |
| 2006/0266361 A1 | 11/2006 | Hernandez | |
| 2007/0125387 A1 | 6/2007 | Zollinger et al. | |
| 2007/0175473 A1 | 8/2007 | Lewis et al. | |
| 2007/0180149 A1 | 8/2007 | Vernal et al. | |
| 2007/0186930 A1 | 8/2007 | Davidson et al. | |
| 2007/0246043 A1 | 10/2007 | Kwok et al. | |

FOREIGN PATENT DOCUMENTS

| | | |
|---|---|---|
| JP | H03505174 A | 11/1991 |
| JP | 2000217916 A | 8/2000 |
| JP | 2001501492 A | 2/2001 |
| JP | 2001507270 A | 6/2001 |
| RU | 2258538 C2 | 8/2005 |
| WO | WO-2007064668 A2 | 6/2007 |

OTHER PUBLICATIONS

European Communication under Rule 71(3) and Text as Proposed for Grant for Application No. 14176016.5, dated Apr. 6, 2016, 52 pages.
Australian Examination Report for Application No. 2006320626, dated Jun. 30, 2011, 2 pages.
Canadian Office Action for Application No. 200680051652.1, dated Feb. 23, 2011, 8 pages.
Canadian Office Action and Examination Search Report for Canadian Application No. 2631808, dated Feb. 20, 2015, 3 pages.
Extended European Search Report for Application No. 06838530.1, dated Mar. 6, 2013, 7 pages.
Extended European Search Report for Application No. 14176016.5, dated Sep. 22, 2014, 9 pages.
International Preliminary Report on Patentability for Application No. PCT/US2006/45616, dated Dec. 7, 2007, 1 page.
Japanese Decision of Refusal for Application No. 2008-543405, dated May 22, 2012, 4 pages.
Japanese Notice of Grant for Application No. 2008-543402, dated Oct. 16, 2012, 3 pages.
Japanese Office Action for Application No. 2008-543402, dated Oct. 25, 2011, 5 pages.
Russian Decision to Grant for Application No. 2008126899, dated Nov. 30, 2010, 13 pages.
European Office Action for Application No. 16180722.7, dated Jan. 25, 2018, 5 pages.

* cited by examiner

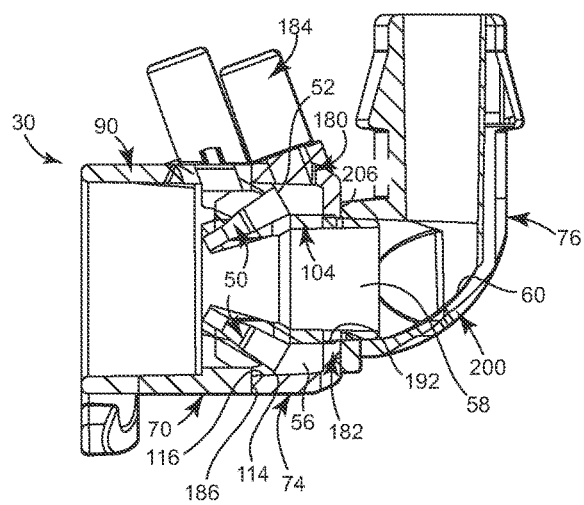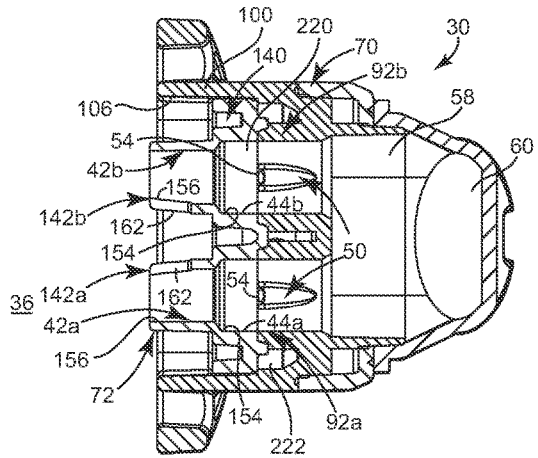
Fig. 8A
Fig. 8B

NASAL CONTINUOUS POSITIVE AIRWAY PRESSURE DEVICE

CROSS-REFERENCE TO RELATED APPLICATIONS

This application is a continuation of Ser. No. 13/967,222, filed on Aug. 14, 2013, which is a continuation of U.S. application Ser. No. 12/547,140, filed on Aug. 25, 2009, and now issued as U.S. Pat. No. 8,534,286, which is a continuation of U.S. application Ser. No. 11/293,883, filed Dec. 2, 2005 and now issued as U.S. Pat. No. 7,578,294, the entire teachings of which are incorporated herein by reference.

BACKGROUND

Field

The present disclosure generally relates to devices and methods for generating and delivering continuous positive airway pressure therapy to patients, such as infants. More particularly, the present disclosure relates to a variable flow, nasal continuous positive airway pressure device, system, and method with improved work of breathing characteristics.

Description of the Related Art

Continuous positive airway pressure (CPAP) therapy has been employed for many years to treat patients experiencing respiratory difficulties and/or insufficiencies. More recently, CPAP therapy has been advanced as being useful in assisting patients with under-developed lungs (in particular, infants and especially premature infants or neonates), by preventing lung collapse during exhalation and assisting lung expansion during inhalation.

In general terms, CPAP therapy entails the continuous transmission of positive pressure into the lungs of a spontaneously breathing patient throughout the respiratory cycle. CPAP can be delivered to the patient using a variety of patient interface devices, for example an endotracheal tube. With infants, however, it is more desirable to employ a less invasive patient interface device, in particular one that interfaces directly or indirectly with the nasal airways via the patient's nares (e.g., mask or nasal prongs). Such systems are commonly referred to as nasal continuous positive airway pressure (nCPAP) systems.

In theory, the CPAP system should deliver a constant, stable pressure to the patient's airways. With conventional, ventilator-based CPAP devices, a relative constant and continuous flow of gas (e.g., air, $O_2$, etc.) is delivered into the patient's airways, with this airflow creating a pressure within the patient's lungs via a restriction placed on outflow from the patient. Unfortunately, this continuous flow can have an adverse effect on the patient's respiratory synchrony. More particularly, the patient is required to exhale against the incoming gas, thus increasing the patient's work of breathing. Control valves can be employed to better accommodate inspiratory and expiratory stages of a patient's breathing (e.g., controlling gas flow into the system and/or altering an extent of restriction to outflow from the system). However, for many patients, especially infants, the ventilator approach is less than satisfactory as the patient's required work of breathing remains quite high. That is to say, it is essentially impossible for a control valve system to accurately replicate the actual respiratory cycles experienced by the patient, such that the patient will consistently be required to exhale against the high momentum, incoming gas, as well as against the resistance of the control valve(s). For an infant with under developed lungs, even a slight increase in the required work of breathing may render the CPAP system in question impractical.

More recently, nCPAP systems have been developed that incorporate a variable flow concept in combination with separate channels for inspiratory and expiratory gas to and from the patient. When the patient inhales, the incoming gas takes the path of least resistance and is directed to the patient's airways. Upon expiration, the gas again takes the path of least resistance and goes out an exhalation or exhaust tube, thus reducing resistance during the expiratory phase. For example, the Infant Flow™ system, available from Viasys Healthcare, Inc., of Conshohocken, Pa., includes a variable flow CPAP generating device (or "CPAP generator") that purportedly causes the direction of the supplied gas to change with the infant's breathing patterns while maintaining a constant pressure throughout the respiratory cycle. The Infant Flow CPAP generator forms two conduits (one for each of the patient's nares), and an exhaust tube. Gas is directed into each respective conduit via an injector nozzle. The momentum of the gas jet acting over the area of the conduit creates a positive pressure inside the patient's lungs, in accordance with known jet pump principles. To accommodate expiratory flow from the patient, the generator relies upon what the manufacturer's literature characterizes as a "fluidic flip" effect. More particularly, the expiratory airflow from the patient applies a pressure onto the incoming flow (within the conduit) from the injector nozzle. It has been theorized that due to the coanda effect, the expiratory airflow causes the nozzle flow to deflect, thus triggering a fluidic flip of the airflow from the nozzle. As a result, fluid flow from the nozzle, as well as the expiratory airflow, readily proceed to the exhaust tube, thus reducing the patient's required work of breathing. While highly promising, current nCPAP products incorporating the "fluidic flip" approach may be less than optimal. For example, the injector nozzle airstream has a relatively high momentum that may not be easily overcome by the patient's expiratory breathing, especially with infants.

In light of the above, a need exists for an improved nCPAP device, system, and method.

SUMMARY

Some aspects in accordance with principles of the present disclosure relate to a nasal continuous positive airway pressure (nCPAP) device for use with an nCPAP system. The device includes a generator body defining a patient side and an exhaust side. The generator body forms at least first and second fluid flow circuits. Each of the fluid flow circuits includes a tube and at least first and second nozzles. The tube defines a passageway forming an axial centerline. The passageway extends from a proximal end of the tube that is otherwise open to the patient side, to a distal end of the tube that is otherwise open to the exhaust side. The first and second nozzles are associated with the tube and each define an inlet end and an outlet end. The inlet end of each of the nozzles is open to a fluid supply, whereas the outlet end, respectively, is open to the passageway. In this regard, each nozzle is adapted to emit a fluid jetstream from the outlet end Along a corresponding flow direction axis. With this in mind, the first and second nozzles are arranged such that the corresponding flow direction axes are non-parallel relative to each other and relative to the corresponding passageway axial centerline. With this configuration, the generator body includes two major passageways each delivering continuous positive pressure to a patient, with each passageway being supplied with fluid via at least two jet flow-inducing nozzles. In one embodiment, the nozzles are arranged relative to the corresponding tube/passageway such that the corresponding flow direction axes, and thus the emitted fluid jetstreams, intersect or impinge upon each other at the axial centerline of the corresponding passageway.

In one non-limiting embodiment, the generator body includes an exhaust port, a jet body, a manifold cover, and an interface plate. The exhaust port forms an exhaust conduit. The jet body forms or provides portions of the fluid flow circuits, including each of the nozzles, distal portions of each of the tubes, and a chamber fluidly connected to the distal portion of the tubes. The manifold cover is assembled between the exhaust port and the jet body. In this regard, the manifold cover forms a supply port. The interface plate forms proximal portions of the first and second tubes and is assembled to the jet body such that the proximal tube portions are fluidly connected to a corresponding one of the distal tube portions so as to complete the first and second tubes. Upon final assembly, the supply port is fluidly connected to each of the nozzles, and the chamber is fluidly connected to the exhaust conduit.

Other aspects of the present disclosure relate to a nasal continuous positive airway pressure (nCPAP) system including a generator body, a fluid supply source, and exhaust tubing. The generator body defines a patient side and an exhaust side, and further forms first and second fluid flow circuits. Each of the fluid flow circuits includes a tube defining a passageway, Along with first and second nozzles fluidly connected to the corresponding passageway. In this regard, relative to each fluid flow circuit, flow direction axes defined by the first and second nozzles are non-parallel relative to an axial centerline defined by the corresponding passageway as well as relative to each other. The fluid supply source is fluidly connected to an inlet end of each of the nozzles, respectively. Finally, the exhaust tubing is fluidly connected to a distal end of each of the passageways, respectively. With this configuration, upon securement of the generator body to a patient's nares, the system is configured to establish a continuous positive airway pressure in the patient by delivering fluid from the fluid supply source to the nozzles. The nozzles, in turn, create a primary fluid jetstream within the corresponding passageway. With this in mind, the system is characterized by an inspiratory phase of operation, in which the primary fluid jetstreams continuously flow toward the patient's nares (capable of entraining gas flow to meet a patient's inspiratory demand), and an expiratory phase of operation in which air exhaled from the patient's nares readily disrupts the fluid jetstreams, thereby reducing the resistance to exhalation flow such that the exhaled air readily flows to the exhaust tubing.

Other aspects in accordance with principles of the present disclosure relate to a method for establishing and delivering continuous positive airway pressure to a patient. The method includes fluidly connecting a generator body to nares of the patient. In this regard, the generator body defines a patient side and an exhaust side, and forms first and second airflow circuits. Each of the airflow circuits includes a tube defining a passageway having a proximal end open to the patient side and a distal end open to the exhaust side. Further, each passageway defines an axial centerline. Each fluid circuit further includes first and second nozzles each defining an inlet end and an outlet end, with the outlet end being open to the corresponding passageway. Further, each nozzle defines a flow direction axis, with the nozzles being arranged such that relative to a respective airflow circuit, the flow direction axes are non-parallel relative to each other and relative to the corresponding passageway axial centerline. With this in mind, fluid is forced from a supply source to the inlet ends of each of the nozzles. A primary fluid jetstream is created within each of the passageways. In particular, the respective first and second nozzles each emit a secondary fluid jetstream into the corresponding passageway and directed towards the patient's nares. The secondary fluid jetstreams impinge upon each other within the corresponding passageway, and combine to form the primary fluid jetstream. The momentum of the jetstreams is converted into pressure. During periods of patient inhalation, the primary fluid jetstreams continuously flow toward the patient's nares, entraining supplemental flow as necessary to meet inspiratory demands. Conversely, during periods of patient exhalation, exhaled air from the patient disrupts the secondary fluid jetstreams so as to eliminate the primary jetstreams, thus minimizing resistance to exhaled airflow. As a result, the exhaled air flows through the passageways to the exhaust side of the generator body. In one embodiment, the secondary fluid jetstreams are characterized as being low momentum jets. In another embodiment, the method is characterized by, during periods of exhalation, the exhaled air from the patient disrupting the secondary jetstreams to generate streamwise vortices that prevent flow separation in the exhalation flow.

BRIEF DESCRIPTION OF THE DRAWINGS

The accompanying drawings are included to provide a further understanding of the present disclosure and are incorporated in and are a part of this specification. Other embodiments of the present disclosure, and many of the intended advantages of the present disclosure, will be readily appreciated as they become better understood by reference to the following detailed description. The elements of the drawings are not necessarily to scale relative to each other. Like reference numerals designate corresponding similar parts.

FIGS. 8A and 8B are cross-sectional views illustrating assembly of the generator body of FIG. 3.

DETAILED DESCRIPTION

Figure 1:
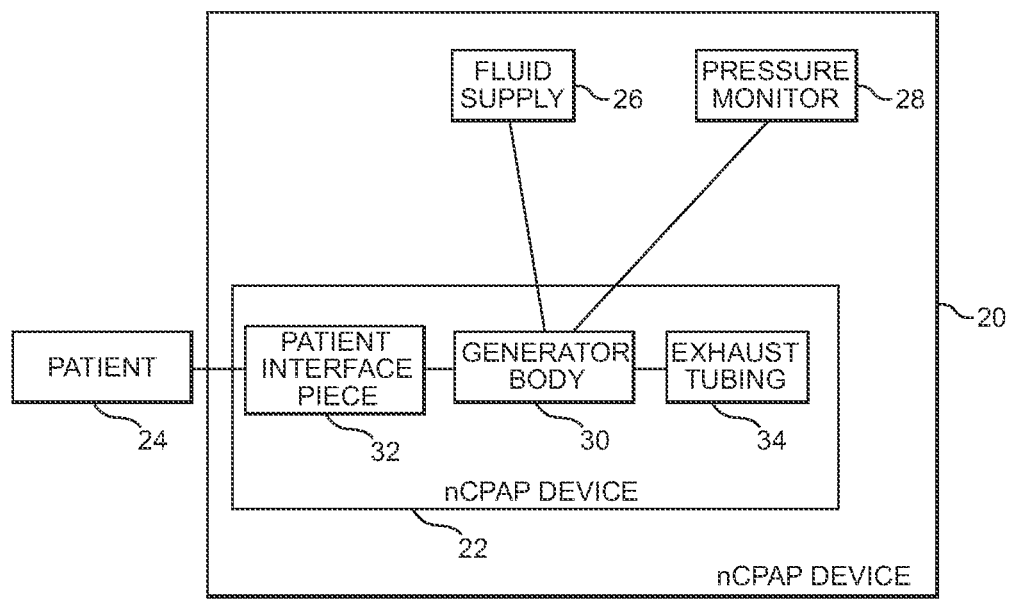
FIG. 1 is a block diagram illustrating one embodiment of a nasal continuous positive airway pressure system including an nCPAP device in accordance with principles of the present disclosure.

One embodiment of an nCPAP system 20 incorporating an nCPAP device 22 in accordance with principles of the present disclosure is shown in block form in FIG. 1. In general terms, the system 20 is adapted to provide CPAP therapy to a patient 24, and includes the nCPAP device 22, a fluid supply 26, and a pressure monitor 28. The nCPAP device 22 is described in greater detail below, and generally includes a generator body 30, a patient interface piece 32, and exhaust tubing 34. The generator body 30 is fluidly connected to both the patient interface piece 32 and the exhaust tubing 34, with the patient interface piece 32 being adapted to establish fluid communication with the patient's 24 nasal airways. The fluid supply 26 provides the generator body 30 with a continuous flow of fluid (e.g., gas such as air and/or oxygen). The pressure monitor 28 is also fluidly connected to the generator body 30 and samples or measures pressure therein. During use, the generator body 30 generates and delivers a continuous positive airway pressure to the patient 24 via the patient interface piece 32. As the patient 24 exhales, the exhaled air readily flows through the patient interface piece 32/generator body 30, and is exhausted from the nCPAP device 22 via the exhaust tubing 34 as described below. As used throughout the specification, directional terminology such as "proximal" and "distal" are used with reference to an orientation of the component in question relative to the patient 24. Thus, "proximal" is closer to the patient 24 as compared to "distal".

Figure 2A:
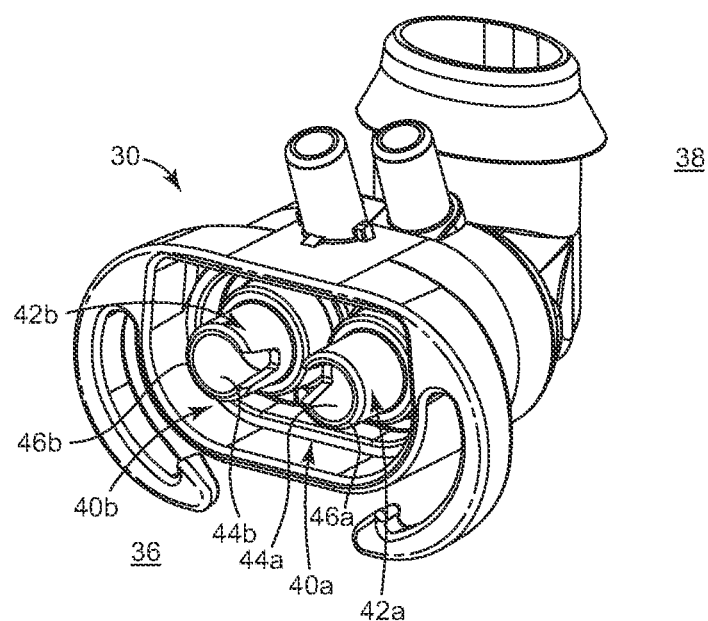
FIG. 2A is a perspective view of an embodiment of a generator body portion of the nCPAP device in accordance with principles of the present disclosure.

One embodiment of the generator body 30 in accordance with principles of the present disclosure is shown in FIG. 2A. The generator body 30 is, in one embodiment, comprised of several interrelated components that combine to form various features. These components are described in greater detail below. Notably, the generator body 30 features can be accomplished via configurations otherwise not including separately formed and subsequently assembled components. Thus, an initial explanation of broader aspects of the generator body 30 is helpful to better appreciate a context of the components relative to the generator body 30 as a whole.

Figure 2B:
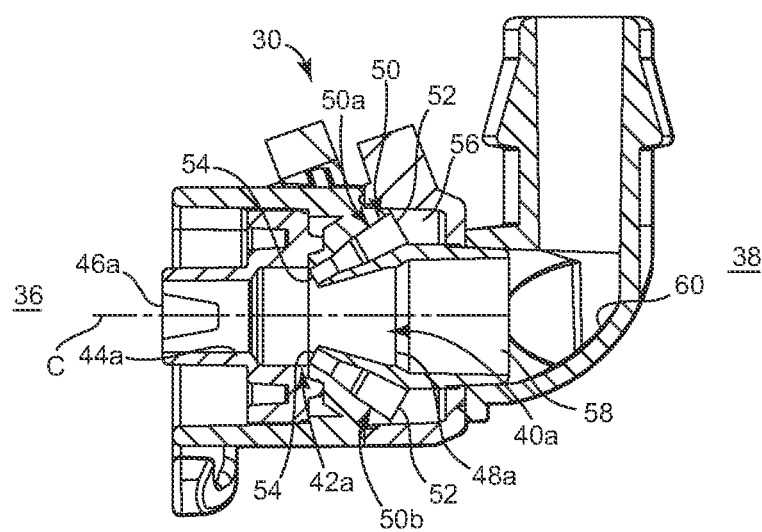
FIG. 2B is a longitudinal cross-sectional view of the generator body of FIG. 2A.

In general terms, the generator body 30 is configured to establish a variable flow CPAP via separate channels for inspiratory and expiratory flow of fluid (e.g., gas) to and from the patient (not shown). Thus, the generator body 30 can be generally described as defining a patient side 36 and an exhaust side 38. With these conventions in mind, and with additional reference to FIG. 2B, the generator body 30 generally defines or forms first and second fluid flow circuits 40a, 40b (referenced generally in FIGS. 2A and 2B; only the first fluid flow circuit 40a is shown in FIG. 2B). The fluid flow circuits 40a, 40b each include a tube 42a, 42b defining a passageway 44a, 44b. The first tube 42a/passageway 44a is shown more clearly in FIG. 2B. The tubes 42a, 42b are arranged in a juxtaposed fashion, extending from an open, proximal end 46a, 46b (i.e., adjacent the patient side 36) to an open, distal end (a distal end 48a of the first tube 42a being shown in FIG. 2B) and defining an axial centerline C (shown for the first fluid flow circuit 40a in FIG. 2B). A plurality of nozzles (hidden in FIG. 2A, referenced generally at 50 in FIG. 2B) are fluidly associated with respective ones of the passageways 44a, 44b. For example, and as best shown in FIG. 2B, the generator body 30 forms first and second nozzles 50a, 50b that are fluidly connected to the passageway 44a defined by the first tube 42a. Though not specifically shown, a similar nozzle arrangement is provided with respect to the passageway 44b defined by the second tube 42b. Regardless, the nozzles 50a, 50b are oriented in a predetermined manner relative to the axial centerline C, as described below.

While the first and second fluid circuits 40a, 40b are shown and described as being identical, in alternative embodiments, the fluid circuits 40a, 40b are not identical in terms of one or more of size, shape, orientation, etc. Similarly, while the fluid circuits 40a, 40b are each described as including two nozzles 50, one or both of the fluid circuits 40a, 40b can include three or more of the nozzles 50. Even further, in other embodiments more than two of the fluid circuits 40a, 40b can be formed. Regardless, and with specific reference to FIG. 2B, each of the nozzles 50a, 50b extends from an inlet end 52 to an outlet end 54, with the outlet end 54 having a reduced diameter as compared to the inlet end 52. The inlet end 52 of each of the nozzles 50a, 50b is fluidly connected to a manifold 56. Finally, the generator body 30 forms a chamber 58 fluidly connecting the open, distal end (e.g., the distal end 48a) of each of the passageways 44a, 44b (FIG. 2A) to an exhaust conduit 60.

With the above general structural features in mind, fluid flow into the manifold 56 is directed through the nozzles 50 that in turn convert the fluid flow into low momentum jetstreams directed into the corresponding tubes 44a, 44b. The so-generated jetstreams are described in greater detail below. Generally, however, a primary jetstream or jet pump is resultingly generated within the passageways 44a, 44b, generally directed toward the patient side 36 (and thus the patient) and creating a continuous positive airway pressure within the passageways 44a, 44b (e.g., the primary jetstream momentum is converted into pressure). Thus, during an inspiratory phase of operation, a continuous positive airway pressure is delivered to the patient. To this end, the primary jetstream is generated so as to enhance entertainment of supplemental gas when required (e.g., when patient's inspiratory demand exceeds set flow of the primary jetstream). Conversely, during an expiratory phase of operation, exhaled air (from the patient) entering the passageways 44a, 44b at the proximal end 46a, 46b, respectively, readily disrupts the jetstreams, effectively eliminating the primary jetstreams. Fluid flow from the nozzles 50 is then caused to fold backwards. As a result, resistance to flow of the exhaled air is minimized, effectively increasing the hydraulic diameter of the flow path. Thus, the exhaled air and fluid flow from the nozzles 50 are directed through the passageways 44a, 44b to the chamber 58/conduit 60.

Figure 3:
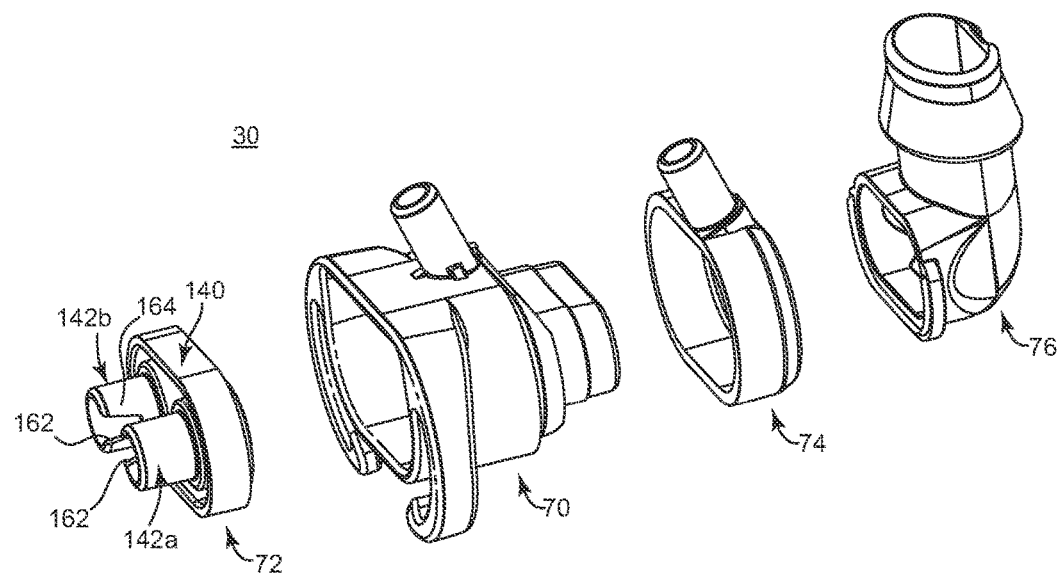
FIG. 3 is an exploded view of one embodiment generator body in accordance with principles of the present disclosure for use as the generator body of FIG. 2A.

With the above principles in mind, components of the generator body 30 in accordance with one embodiment are shown in greater detail in exploded view of FIG. 3. The generator body 30 includes a jet body 70, an interface plate 72, a manifold cover 74, and an exhaust port 76. In general terms, the manifold cover 74 is disposed between the jet body 70 and the exhaust port 76, and combines with the jet body 70 to form the manifold 56 (FIGS. 2A and 2B). The interface plate 72 is assembled to the jet body 70, with the jet body 70/interface plate 72 combining to define the tubes 42a, 42b/passageways 44a, 44b (FIG. 2B). The interface plate 72 is further configured to provide fluid connection to the patient interface piece 32 (FIG. 1). Conversely, the exhaust port 76 fluidly connects passageways formed by the jet body 70/interface plate 72 to the exhaust tubing 34 (FIG. 1).

The jet body 70 is shown in greater detail in FIGS. 4A-4D. In one embodiment, the jet body 70 includes a housing 90 forming or surrounding first and second distal tubular members 92a, 92b as well as the chamber 58. As described in greater detail below, the distal tubular members 92a, 92b define distal segments of the tubes 42a, 42b (FIG. 2A) upon final assembly with the interface plate 72 (FIG. 3). Further, the housing 90 defines or surrounds the nozzles 50 (referenced generally in FIGS. 4A and 4B). Finally, in one preferred embodiment, the jet body 70 further includes an intermediate wall 94, a pressure monitoring port 96, and mounting features 98 (best shown in FIG. 4A). As described below, the intermediate wall 94 fluidly isolates the chamber 58 from portions of the jet body 70 proximal thereof. The pressure monitoring port 96 is located to tap or sample air pressure within the generator body 30 (FIG. 2A). Finally, the mounting features 98 provide a means for securing the jet body 70, and thus the assembled generator body 30, to a patient.

Figure 4A:
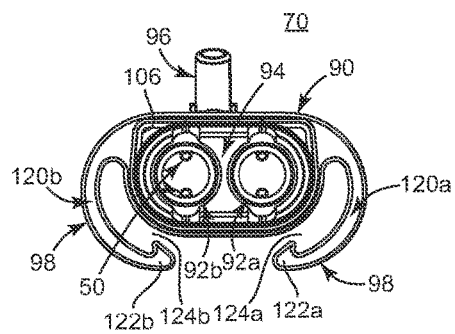
FIG. 4A is a front view of a jet body component of the generator body of FIG. 3.
Figure 4C:
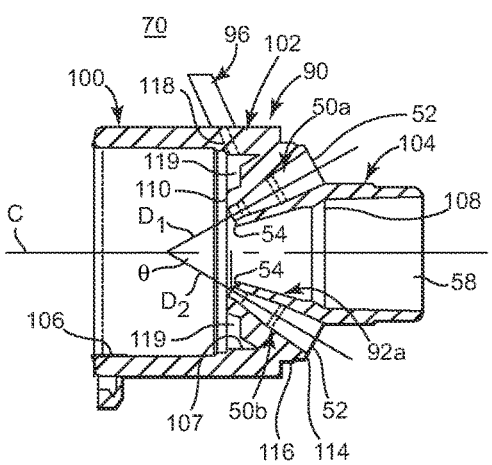
FIG. 4C is a top cross-sectional view of the jet body of FIG. 4A.
Figure 4B:
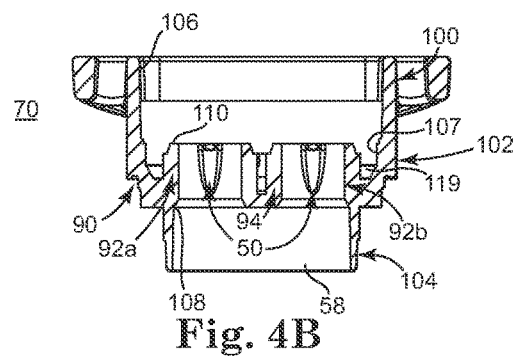
FIG. 4B is a side cross-sectional view of the jet body of FIG. 4A.

Commensurate with the above description and with specific reference to FIGS. 4B and 4C, the housing 90 can be described as defining a proximal segment 100, an intermediate segment 102, and a distal segment 104. The segments 100-104 are continuous, and each define certain features of the jet body 70, including promoting assembly to other components.

For example, the proximal segment 100 forms an opening 106 sized to receive and maintain the interface plate 72 (FIG. 3) as well as a portion of a patient interface piece (not shown). In one embodiment, the proximal segment 100, and thus the opening 106, is generally oval-like in a front planar view (FIG. 4A), although other shapes are also acceptable. Further, a shape of the opening 106 can also have certain, non-symmetrical attributes that promote assembly of the patient interface piece at a desired orientation relative to the jet body 70, as described below.

The intermediate segment 102 forms or maintains the distal tubular members 92a, 92b, and the nozzles 50 (as best shown in FIG. 4B). In one embodiment, the nozzles 50 are molded in (or formed by) the intermediate segment 102 (and thus the jet body 70). As compared to a CPAP generator configuration in which the jet-producing nozzle is formed apart from, and subsequently assembled to, a primary conduit housing, the integrally molded nozzles 50 are less likely to leak during use (that in turn might otherwise expose the patient to higher-than or lower-than expected pressure conditions). Alternatively, however, the nozzles 50 can be separately formed. In addition, the intermediate segment 102 defines an interior surface 107.

The distal segment 104 defines the chamber 58, with the intermediate segment 102 and the distal segment 104 being separated by the intermediate wall 94. In addition, an exterior of the intermediate segment 102 and distal segment 104 is configured to be received by, and for attachment to, the manifold cover 74 (FIG. 3) as described below.

Relative to the above explanation of the housing 90, the distal tubular members 92a, 92b are, in one embodiment, identical, such that the following description of the first distal tubular member 92a Along with its relationship to the corresponding nozzles 50 applies equally to the second distal tubular member 92b and the corresponding nozzles 50. With this in mind, the distal tubular member 92a extends from a distal side 108 formed in the intermediate wall 94 to a proximal side 110 that is otherwise laterally spaced from the interior surface 107 of the housing intermediate segment 102. A majority of the distal tubular member 92a is substantially uniform in diameter, expanding slighting at the distal side 108 (that is otherwise fluidly open to the chamber 58). This expansion in diameter promotes laminar fluid flow from the distal tubular member 92a into the chamber 58. By way of example, but in no way limiting, the distal tubular member 92a has an inner diameter on the order of 0.194 inch, with each of the nozzles 50a, 50b (FIG. 4C) projecting into this so-defined diameter.

Further, the distal tubular member 92a defines the axial centerline C (it being understood that the axial centerline C shown in FIG. 4C is also the axial centerline C (FIG. 2B) of the passageway 42a (FIG. 2B) upon final assembly with the interface plate 72 (FIG. 3)). As shown, the nozzles 50a, 50b are fluidly open to the distal tubular member 92a at the proximal side 110 and are arranged in a non-parallel fashion relative to the axial centerline C, as well as to each other. More particularly, the nozzles 50a, 50b are formed at circumferentially opposite sides of the tubular portion 92a such that the respective outlet ends 54 each project into the distal tubular member 92a. The nozzles 50a, 50b each define a flow direction axis D1, D2. The flow direction axes D1, D2 corresponds with the central axis defined by the respective nozzles 50a, 50b, and define the direction in which fluid exits from the respective outlet end 54 thereof. With this in mind, in one embodiment, the nozzles 50a, 50b are arranged such that the flow direction axes D1, D2 intersect or impinge upon each other approximately at the axial centerline C. That is to say, the nozzle 50a, 50b are symmetrically arranged about the axial centerline C. To this end, and in one embodiment, the nozzles 50a, 50b are angularly oriented relative to the axial centerline C such that the flow direction axes D1, D2 combine to define an included angle $\Theta$ in the range of 40°-80°, preferably 50°-70°, more preferably approximately 60° (±1°). In addition, each of the nozzles 50a, 50b are configured to generate jetstream fluid flow via a constricted fluid flow path from the inlet end 52 to the outlet end 54. For example, in one embodiment, the inlet end 52 has a diameter of approximately 0.069 inch, whereas an outlet end 54 has a diameter of approximately 0.0245 inch (it being understood that a wide variety of other dimensions are equally acceptable). Regardless, fluid jetstreams produced by the nozzles 50a, 50b impinge upon one another and combine approximately at the axial centerline C. In alternative embodiments, three or more of the nozzles 50 can be associated with the distal tubular member 92a, disposed at various circumferential locations about the distal tubular member 92a; with many of these alternative embodiments, however, the corresponding flow directions axes established by each of the multiplicity of nozzles 50 all impinge upon one another at approximately the axial centerline C. In other alternative embodiments, the nozzles 50 are located and/or oriented in an offset relationship such that the corresponding flow direction axes D1, D2 intersect at a point away from the axial centerline C. This configuration will induce swirling during an expiratory mode of operation, as described below.

Figure 4D:
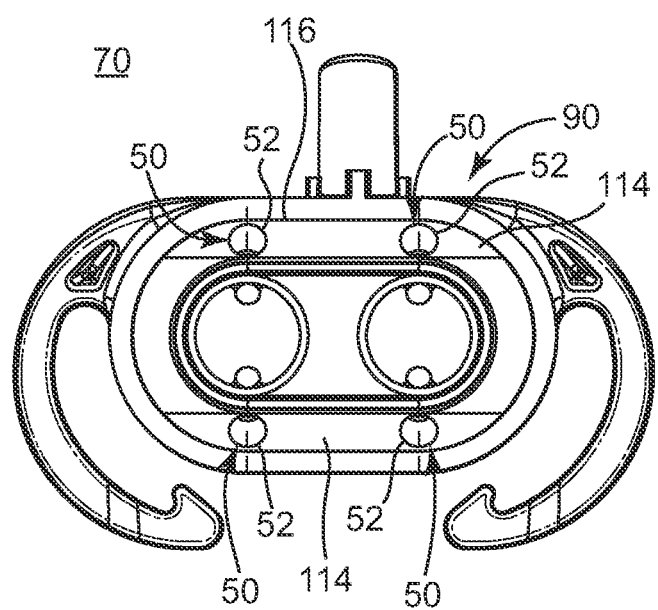
FIG. 4D is a rear view of the jet body of FIG. 4A.

In addition to defining or surrounding the outlet ends 54 of the nozzles 50, the housing intermediate segment 102 also forms the inlet ends 52 thereof such that the inlet ends 52 are open to an exterior of the housing 90. For example, in one embodiment, an exterior of the intermediate segment 102 includes a rear surface 114 and a ledge 116. The rear surface 114 extends in an angular fashion (tapering in transverse cross-sectional area) from the ledge 116 to the distal segment 104. As shown in FIG. 4D, the inlet end 52 of each of the nozzles 50 extends through, and is fluidly open relative to, the rear surface 114, with the ledge 116 providing a surface for assembly of the manifold cover 74 (FIG. 3). Thus, the rear surface 114 completes the manifold 56 (FIG. 2B) upon final assembly of the manifold cover 74 to the jet body 70 as described below.

With the above description of the housing 90 in mind, in one embodiment and as best shown in FIG. 4C, the pressure monitoring port 96 extends from the housing 90 and forms an aperture 118 (shown with dashed lines) extending through the intermediate segment 102. The aperture 118 is open to an interior of the housing 90 proximal the intermediate wall 94 (FIG. 4B), and in particular to a volumetric spacing 119 (referenced generally) between the distal tubular members 92a, 92b and the interior surface 107 of the housing intermediate segment 102. As described in greater detail below, this location, in conjunction with features of the interface plate 72 (FIG. 3), facilitates tapping or measurement of pressure within the jet body 70/generator body 30 (FIG. 2A).

Finally, and returning to FIG. 4A, the mounting features 98 include, in one embodiment, a pair of flanges 120a, 120b extending in an opposing fashion from the housing proximal segment 100, each terminating in a clip 122a, 122b, respectively. Each clip 122a, 122b is spaced from the housing 90 to establish a gap 124a, 124b. The gaps 124a, 124b are sized to slidably receive a strap (not shown) otherwise used to secure the generator body 30 (FIG. 2A) to a patient. The clips 122a, 122b provide a surface for frictionally engaging the strap. Alternatively, the mounting features 98 can assume a variety of other forms, and in some embodiments are eliminated.

Figure 5A:
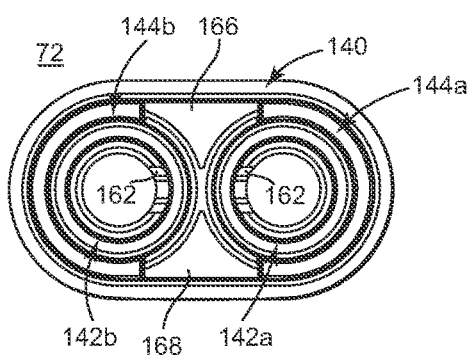
FIG. 5A is a front view of an interface plate component of the generator body of FIG. 3.
Figure 5C:
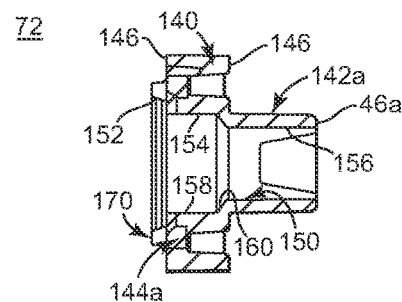
FIG. 5C is a side cross-sectional view of the interface plate of FIG. 5A.
Figure 5B:
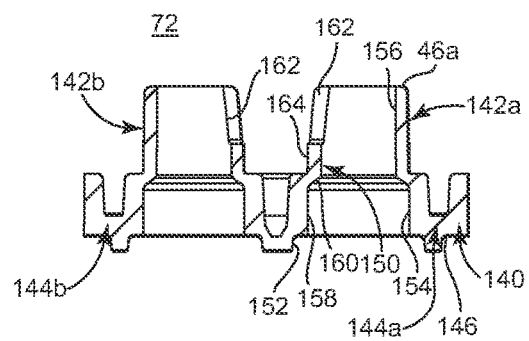
FIG. 5B is a top cross-sectional view of the interface plate of FIG. 5A.

Returning to FIG. 3, and with additional reference to FIGS. 5A-5C in one embodiment, the interface plate 72 includes a frame 140, first and second proximal tubular members 142a, 142b, and first and second connection bodies 144a, 144b. In general terms, the connection bodies 144a, 144b partially extend between the respective proximal tubular members 142a, 142b and the frame 140 so as to laterally space the proximal tubular members 142a, 142b from the frame 140.

The frame 140 is sized to nest within the opening 106 (FIG. 4A) of the jet body 70. Thus, in one embodiment, the frame 140 has a generally oval-like shape (best shown in FIG. 5A), terminating in a relatively flat rear surface 146 (FIGS. 5B and 5C) adapted for a sealing fit or assembly (e.g., welding) to the jet body housing 90 (FIG. 4A). Alternatively, the frame 140 can assume a variety of other forms.

In one embodiment, the proximal tubular members 142a, 142b are juxtaposed and identically formed, such that the following description of the first proximal tubular member 142a applies equally to the second proximal tubular member 142b. With this in mind and with specific reference to FIGS. 5B and 5C, the proximal tubular member 142a forms a passage 150 and is defined by a distal region 152, an intermediate region 154, and a proximal region 156. The proximal region 156 terminates at the proximal end 46a (otherwise corresponding or defining the proximal end 46a of the tube 42a (FIG. 2A) upon final assembly). Conversely, the distal region 152 is sized and shaped for assembly over a corresponding one of the distal tubular members 92a, 92b (FIG. 4B) of the jet body 70. Thus, an inner diameter of the distal region 152 is greater than an outer diameter of the corresponding distal tubular member 92a or 92b. Notably, in one embodiment, the distal region 152 extends distally beyond the rear surface 146 of the frame 140 for establishing a pressure chamber (not shown) upon final assembly to the jet body 70 as described below.

The intermediate region 154 extends from, and has a reduced inner diameter as compared to that of, the distal portion 152, and in one embodiment includes a first portion 158 and a second portion 160. The second portion 160 tapers in diameter from the first portion 158 to the proximal region 156. More particularly, an inner diameter of the first portion 158 corresponds with a diameter of the corresponding distal tubular member 92a (FIG. 4C), and is greater than an inner diameter of the proximal region 156. As described in greater detail below, this enlarged area accommodates and promotes disruption of jetstream(s) during use. By way of example, but in no way limiting, an inner diameter of the first portion 158 is on the order of 0.194 inch, whereas an inner diameter of the proximal region 156 is on the order of 0.142 inch. Alternatively, a wide variety of other dimensions are equally acceptable, so long as at least a portion of the intermediate region 154 (i.e., the first portion 158) has an inner diameter greater than that of the proximal region 156. Along these same lines, a longitudinal length of the first portion 158 corresponds with an angular orientation and traverse offset distance between the nozzles 50a, 50b (FIG. 4C) otherwise associated with the distal tubular member 92a to which the proximal tubular member 142a is assembled. More particularly, the first portion 158 is sized such that upon final assembly, the jetstreams generated by the nozzles 50 impinge upon each other proximate or within the second portion 160 and/or the proximal region 156 (i.e., region with reduced diameter) to ensure formation of a primary jetstream or jet pump. In one embodiment, but in no way limiting, the first portion 158 has a longitudinal length of approximately 0.134 inch.

Finally, the proximal region 156 extends proximally outwardly relative to the frame 140 and defines a surface for receiving a corresponding portion of the patient interface piece 32 (FIG. 1). In one embodiment, and as best shown in FIGS. 3 and 5B, a radial slot 162 is formed Along an interior side 164 of the proximal tubular member 142a (i.e., the side facing the opposing proximal tubular member 142b), extending from the proximal end 46a. The radial slot 162 is sized in accordance with the patient interface piece 32 (FIG. 1) and, as described below, provides a region from which pressure otherwise present within the proximal tubular member 142a can be tapped or sampled. In one embodiment, the radial slot 162 has a longitudinal length on the order of 0.05-0.5 inch, although other dimensions are equally acceptable. In other embodiments, dimension(s) of the slot 162 are correlated with an inner diameter of the tubular member 142a at the proximal end 64 thereof. It has been surprisingly discovered that pressure being delivered to a patient can be sampled with high accuracy but with minimal or no occurrences of back pressure generation by forming the radial slot 162 to have a length that is no more than 85% of the inner diameter of the tubular member 142a at the proximal end 64 and/or a width that is no less than 25% of the inner diameter of the tubular member 142a at the proximal end 64. Regardless, the second proximal tubular member 142b similarly forms the radial slot 162 (Along a side facing the first proximal tubular member 142a).

Finally, the connector bodies 144a, 144b extend from a portion of a circumference of the corresponding proximal tubular member 142a, 142b. In this regard, and as best shown in FIG. 5A, first and second pressure taps or cutouts 166, 168 are defined between the connector bodies 144a, 144b. The cutouts 166, 168 establish a fluid connection between the radial slots 162 and a rear face 170 (referenced generally in FIG. 5B) of the interface plate 72. As described below, the cutouts 166, 168 facilitate tapping or sampling of pressure within the generator body 30 (FIG. 2A) upon final assembly.

Figure 6A:
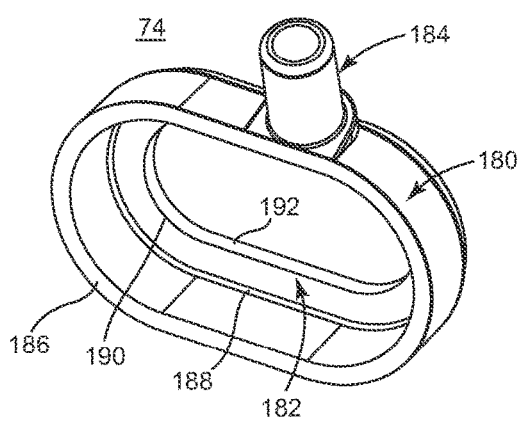
FIG. 6A is a front perspective view of a manifold cover component of the generator body of FIG. 3.
Figure 6B:
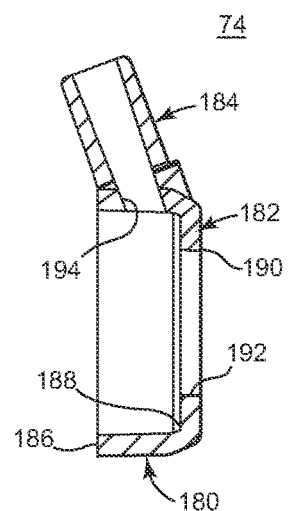
FIG. 6B is a side cross-sectional view of the manifold cover of FIG. 6A.

With reference to FIGS. 6A and 6B, in one embodiment the manifold cover 74 includes a side wall 180, a partition 182, and a supply port 184. The side wall 180 forms a continuous, tubular body that extends from a front side 186 to a rear side 188. In this regard, the side wall 180 is sized for assembly about a portion of the jet body housing 90 (FIG. 4A) and thus has, in one embodiment, an oval-like shape in transverse cross-section.

The partition 182 extends radially inwardly from the rear side 188 of the side wall 180, terminating at an edge 190 that defines an opening 192. The opening 192 is fluidly open to an interior of the side wall 180 and is sized to receive the distal segment 104 of the housing 90 (FIG. 4C). Thus, in one embodiment, the edge 190/opening 192 defines an oval-like shape.

Finally, and with specific reference to FIG. 6B, the supply port 184 extends outwardly from the side wall 180, forming an aperture 194 through a thickness thereof. The support port 184 is configured for assembly to, and fluid connection with, tubing (not shown), such as tubing extending from a fluid supply source. With this construction, then, the supply port 184 provides fluid connection between a fluid supply source an interior of the side wall 180. As described below, the supply port 184 thus facilitates delivery of fluid flow to the generator body 30 (FIG. 2A).

Figure 7A:
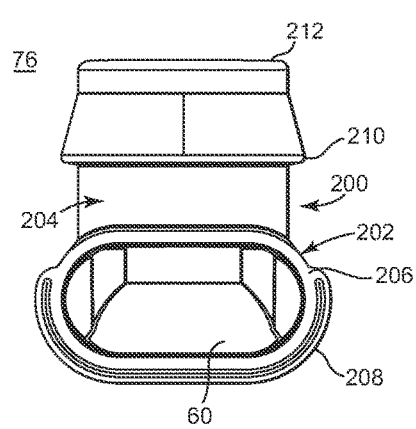
FIG. 7A is a front view of an exhaust port component of the generator body of FIG. 3.
Figure 7B:
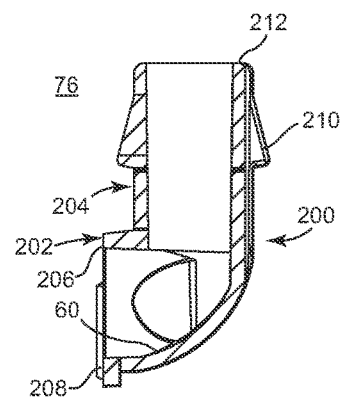
FIG. 7B is a side cross-sectional view of the exhaust port of FIG. 7A.
Figure 7C:
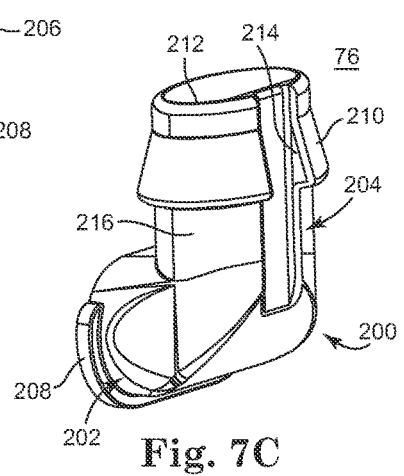
FIG. 7C is a rear perspective view of the exhaust port of FIG. 7A.

The exhaust port 76 is shown in greater detail in FIGS. 7A-7C. The exhaust 76 includes a conduit body 200 forming the conduit 60 previously described. In one embodiment, the conduit body 200 includes a first segment 202 and a second segment 204. The first segment 202 extends in a generally longitudinal fashion from a front face 206 otherwise including, in one embodiment, a partial rim 208. The partial rim 208 is best shown in FIG. 7A and provides an enlarged surface that facilitates assembly to the manifold cover partition 182 (FIG. 6A), such as via welds. Regardless, the front face 206 is sized and shaped to receive the distal segment 104 of the housing 90 (FIG. 4A) to establish a fluid connection between the chamber 58 (FIG. 4A) and the conduit 60.

The second segment 204 extends from the first segment 202 opposite the front face 206, defining a bend in the range of 70°-110°, for example approximately 90° in one embodiment. With this one construction, the exhaust port 76 promotes extension of associated exhaust tubing (not shown) in a desired direction away from the exhaust port 76, and thus relative to the generator body 30 (FIG. 2A). To this end, in one embodiment, the second segment 204 forms a circumferential barb 210 adjacent a trailing face 212 thereof. The barb 210 is configured to facilitate securement of the exhaust tubing to the exhaust port 76 in a manner that allows the exhaust tubing to be rotated about the barb 210. Alternatively, the exhaust port 76 can incorporate various other structures that promote securement of the exhaust tubing, such that the circumferential barb 210 can be eliminated. Along these same lines and with particular reference to FIG. 7C, in one embodiment, the second segment 204 forms a groove 214 Along a rear side 216 thereof. The groove 214 facilitates release of excess pressure from within the exhaust port 76/exhaust tubing during use. Alternatively, the groove 214 can be eliminated. While the first segment 202 and the second segment 204 have been illustrated as being rigidly connected, in alternative embodiments the exhaust port 76 is configured such that the second segment 204 is rotatably coupled to the first segment 202. With this configuration, a user can swivel the second segment 204 (and thus the exhaust tubing attached thereto) relative to the first segment 202 (and thus a remainder of the generator body 30) to a desired spatial location.

Assembly of the generator body 30 in accordance with principles of the present disclosure can be described with reference to FIGS. 8A and 8B. In this regard, while the components 70-76 are described as being assembled in a particular order, this is in no way limiting. With specific reference to FIG. 8A, the manifold cover 74 is assembled to the jet body 70. More particularly, the distal segment 104 of the housing 90 of the jet body 70 is received within, and passes through, the opening 192 defined by the partition 182 of the manifold cover 74. The front side 186 of the side wall 180 abuts against the ledge 116 of the jet body housing 90 such that the rear surface 114 of the jet body housing 90, and thus the inlet ends 52 of the nozzles 50, are within the interior region defined by the side wall 180. The manifold cover 74 is then affixed to the jet body 70, such as by ultrasonically welding the front side 186 of the side wall 180 to the ledge 116 of the jet body housing 90. Upon final assembly, the jet body housing 90 and the side wall 180 combine to define the manifold 56. More particularly, assembly of the manifold cover 74 to the jet body 70 establishes a fluid seal about the manifold 56, thus establishing a fluid connection between the supply port 184 and the inlet end 52 of each of the nozzles 50. That is to say, the manifold cover 74 extends about an entirety of the distal segment 104 of the jet body housing 90, such that each of the nozzles 50 are fluidly connected to the single manifold 56 that in turn is fluidly connected to the supply port 184.

The exhaust port 76 is then assembled over the distal segment 104 of the jet body housing 90 such that the conduit 60 is fluidly connected to the chamber 58. In one embodiment, the front face 206 of the exhaust port conduit body 200 is abutted against, and affixed to (e.g., welded), the manifold cover partition 182 and/or an exterior of the distal segment 104 of the housing 90 thus establishing a fluid-tight seal.

With reference to FIG. 8B, the interface plate 72 is assembled to the jet body 70. More particularly, the interface plate frame 140 nests within the opening 106 of the housing proximal segment 100, with the proximal tubular members 142a, 142b of the interface plate 72 being assembled to, and fluidly connected with, a respective one of the distal tubular members 92a, 92b of the jet body 70. Thus, upon final assembly of the interface plate 72 to the jet body 70, the first proximal and distal tubular members 142a, 92a combine to define the first tube 42a, and the second proximal and distal tubular members 142b, 92b combine to define the second tube 42b. In this regard, a fluid-tight seal (e.g., no fluid leakage at 3 psi) is established between the corresponding tubular members 142a/92a and 142b/92b, such as via welding of the interface plate 72 to the jet body 70. Regardless, each of the so-constructed tubes 42a, 42b forms the corresponding passageways 44a, 44b that are both fluidly connected to the chamber 58 that in turn is fluidly connected to the conduit 60. Further, at least two of the nozzles 50 (referenced generally) project within, and are fluidly connected to, a corresponding one of the passageways 44a, 44b, with the flow direction axes D (FIG. 4C) defined by the corresponding nozzles 50 intersecting or impinging upon one another approximately at, in one embodiment, the axial centerline C (FIG. 4C) of the passageway 44a or 44b. Once again, the intermediate and proximal regions 154, 156 of the proximal tubular portions 142a and 142b form the resultant tube 42a or 42b to have a larger inner diameter proximate the corresponding nozzle outlet ends 54 (i.e., Along the first portion 158 (FIG. 4C)) as compared to an inner diameter further downstream of the outlet ends 54 (i.e., Along the second portion 160 and the proximal region 156). By way of reference, this increased diameter (and thus increased volume) is reflected in FIG. 8B as a relief zone 220 within each of the tubes 42a, 42b.

Further, a spacing or pressure chamber 222 (referenced generally) is established between the jet body housing 90, the interface plate frame 140, and exteriors of each of the proximal and distal tubular members 142/92. The pressure chamber 222 is fluidly open at the cutouts 166, 168 (hidden in FIG. 8B, but shown in FIG. 5A), and is fluidly connected to the pressure monitoring port 96 (FIG. 4C). As described below, pressure within the generator body 30 adjacent the patient side 36 thereof is transmitted to the pressure chamber 222. The pressure chamber 222 provides a means for venting pressure from the pressure taps or cutouts 166, 168 (FIG. 5A) to the pressure monitoring port 96 for measuring the pressure within the generator body 30. As clarified below, the radial slots 162 define the locations from which pressure in the tube 42a, 42b is sampled. Notably, because the radial slots 162 are located at the proximal end of the respective tubes 42a, 42b (and thus as close as possible to the patient interface piece (not shown)), and further because the cutouts 166, 168 are in close proximity to the radial slots 162 (e.g., on the order of 0.2 inch in one embodiment), a more accurate evaluation of pressure actually being delivered to the patient can be made as compared to conventional nCPAP generator configurations.

In one embodiment, each of the generator body components 70-76 are molded from a similar plastic material amenable to subsequent assembly via welding. For example, in one embodiment, each of the generator body components 70-76 are molded polycarbonate, although other plastic materials such as acrylic resins or acrylic copolymer resins, other thermoplastic materials, etc., are also acceptable. Along these same lines, affixment of the components 70-76 to one another is characterized by a fluid-tight seal in which leakage does not occur at pressures of 3 psi. For example, welding (e.g., ultrasonic welding), adhesives, etc., can be employed. Alternatively, two or more of the components 70-76 can be integrally formed; for example, in one alternative embodiment, the generator body 30 can be molded or formed as a single, integral piece. It has been surprisingly found, however, that by forming the components 70-76 separately from one another, tight tolerances on the primary features of the generator body 30 as a collective whole can be achieved while minimizing an overall size thereof. Further, in the one embodiment described above, the components 70-76 are assembled in a stacked manner. All interface planes between adjacent components are essentially perpendicular to the direction of fluid flow toward the patient during use. Thus, any leaks that may occur between adjacent components 70-76 are not open to the patient fluid flow, but instead flow to an exterior of the generator body 30. This, in turn, prevents occurrences of high pressure leaks to the patient.

Figure 8C:
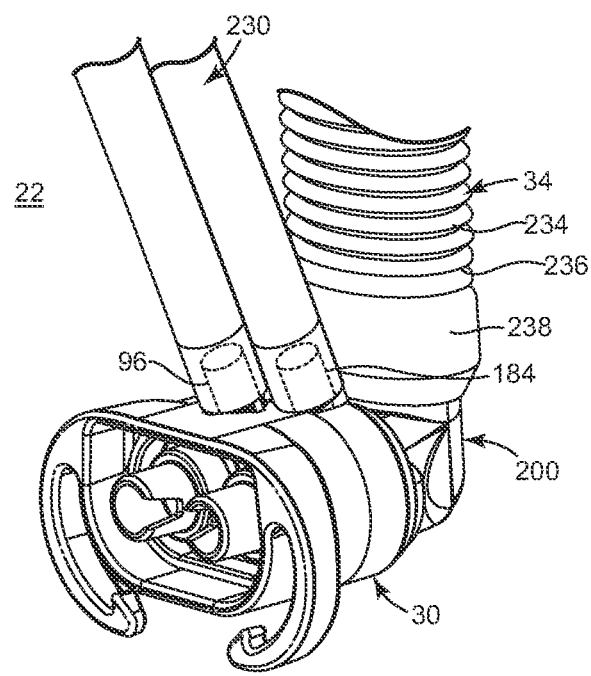
FIG. 8C is a perspective view of an nCPAP device in accordance with principles of the present disclosure, including the generator body of FIG. 3.

The assembled generator body 30 can then be provided with additional components in forming the nCPAP device 22 as shown in FIG. 8C. For example, a fluid supply tube 230 is fluidly connected at one end to the supply port 184 and at an opposite end (not shown) to the fluid supply (not shown), such as a pressurized source of gas (e.g., air, oxygen, etc.). Similarly, vent tubing 232 is fluidly connected at one end to the pressure monitoring port 96 and at an opposite end (not shown) to a pressure monitoring device (not shown). As previously mentioned, the pressure monitoring port 96 is open to fluid pressure within the generator body 30 such that the pressure monitoring device can determine the level of pressure being delivered to the patient via the vent tubing 232. Finally, the exhaust tubing 34 is assembled over, and fluidly connected to, the exhaust port conduit body 200. In one embodiment, the circumferential barb 210 (FIG. 7A) provides longitudinally locked securement of the exhaust tubing 34 to the exhaust port 76. In one embodiment, the exhaust tubing 34 has a corrugated or accordion-like configuration (e.g., corrugated, expandable/collapsible tubing), such that the exhaust tubing 34 can be readily oriented (e.g., bent) in a desired manner without effectuating a "pinch" in the exhaust tubing 34. In a further embodiment, the exhaust tubing 34 defines a primary corrugated segment 234, a relief segment 236, and a leading end 238 as shown in FIG. 8C. The leading end 238 is configured for placement over, and securement to, the exhaust port 76 and thus is free of corrugations. The primary corrugated segment 234 extends Along a majority of the tubing 34, and is structurally formed to expand or contract as desired and dictated by the user, maintaining the expanded or contracted length. Conversely, while the relief segment 236 includes inwardly and outwardly extending wall portions for easy expansion and contraction, it is of a reduced wall thickness and is highly flexible (as compared to the corrugated segment 234). This promotes an ability of a user to rotate the exhaust tubing 34 relative to the exhaust port 76, yet the exhaust tubing 34 remains longitudinally locked to the exhaust port 76. Alternatively, the exhaust tubing 34 (as well as the fluid supply tube 230 and the vent tubing 232) can assume a variety of other forms. For example, the exhaust tubing 34 one or all of the tubing 34, 230, and/or 232 can be formed of a rigid yet malleable material that can be repeatedly bent to a desired shape by a user, and independently maintain the bent shape. As a point of reference, a length of each of the tubing 34, 230, and 232 is attenuated in the view of FIG. 8C for ease of illustration.

Figure 9A:
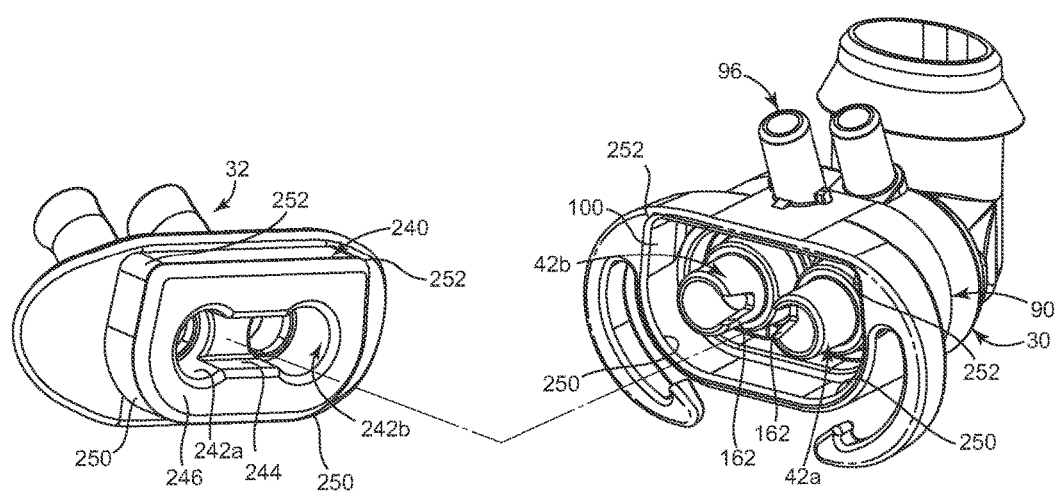
FIG. 9A is a perspective, exploded view of the generator body of FIG. 3 in combination with one embodiment of a patient interface piece.
Figure 9B:
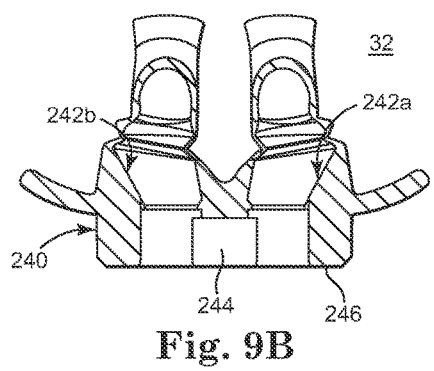
FIG. 9B is a bottom cross-sectional view of the patient interface piece of FIG. 9A.

Prior to use of the nCPAP system 20 (FIG. 1), the patient interface piece 32 is assembled to the nCPAP device 22, and in particular the generator body 30, as shown in FIGS. 9A and 9B. The patient interface piece 32 can assume a variety of forms suitable for establishing fluid connection to a patient's nasal airways (not shown). Thus, the patient interface piece 32 can include an opposing pair of nasal prongs as shown. Alternatively, the patient interface piece 32 can be a mask otherwise establishing a singular fluid connection of the generator body 30 to both of the patient's nasal airways. Regardless, in one embodiment, the patient interface piece 32 includes a base 240 formed of a resilient, compliant material and is configured to interact with certain features of the generator body 30 as described below.

For example, in one embodiment the base 240 forms a pair of lumens 242a, 242b extending through a thickness of the base 240, as well as a channel 244 extending between the lumens 242a, 242b. The channel 244 and the lumens 242a, 242b are open relative to a distal face 246 of the base 240, with the channel 244 having a longitudinal length corresponding with that of the radial slot 162 associated with each of the tubes 42a, 42b of the generator body 30. With this in mind, assembly of the patient interface piece 32 to the generator body 30 includes mounting respective ones of the tubes 42a, 42b within a respective one of the lumens 242a, 242b. The base 240 is further lodged within the proximal segment 100 of the jet body housing 90 such that the base 240 is frictionally secured between the jet body housing 90 and the tubes 42a, 42b.

In this regard, in one embodiment, a shape of the base 240 corresponds with a shape of the proximal segment 100 of the jet body housing 90. In one preferred embodiment, the corresponding shapes are non-symmetrical to ensure a desired orientation of the patient interface piece 32 relative to the generator body 30. For example, in one embodiment, the base 240 and the proximal segment 100 of the jet body housing 90 include a pair of arcuate or generally curved corners 250, and a pair of relatively distinct or "sharp" corners 252 as shown in FIG. 9A (i.e., the curved corners 250 have a larger radius of curvature as compared to the sharp corners 252). With this configuration, the patient interface piece 32 cannot be accidentally assembled to the generator body 30 in an orientation opposite that shown in FIG. 9A. Alternatively, the patient interface 32 can assume a variety of other forms that may or may include a non-symmetrically shaped base 240.

Figure 9C:
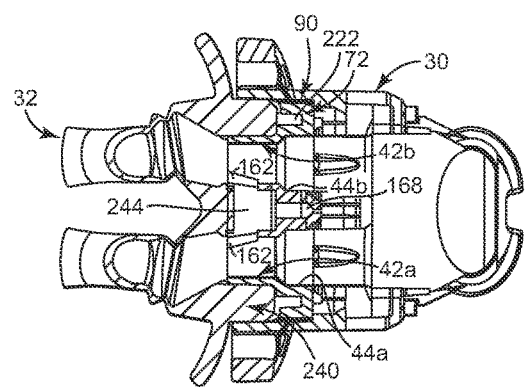
FIG. 9C is a bottom cross-sectional view of the combination generator body and patient interface piece of FIG. 9A upon final assembly.

Regardless, in one embodiment, the patient interface piece 32 is configured to maintain a desired fluid connection between the proximal segment 100 of the jet body housing 90 and the pressure monitoring port 96. In particular and with reference to FIG. 9C, assembly of the base 240 to the tubes 42a, 42b of the generator body 30 is such that the channel 244 is open relative to the radial slot 162 defined by each of the tubes 42a, 42b. Thus, fluid flow within the passageways 44a, 44b can flow outwardly therefrom via the radial slots 162 and the channel 244. Further, fluid flow from the channel 244 is permitted to flow to and through the pressure taps or cutouts 166, 168 (it being understood that only the cutout 168 exists in the sectional view of FIG. 9C; the cutout 166 is illustrated in FIG. 5A) defined by the interface plate 72. The cutouts 166, 168, in turn, are fluidly open to the pressure chamber 222 defined between the interface plate 72 and the proximal segment 100 of the jet body housing 90. Thus, a pressure monitoring fluid circuit is established by a fluid connection of the pressure monitoring port 96 (FIG. 9A) and the passageways 44a, 44b via the radial slots 162, the channel 244, the cutouts 166, 168, and the pressure chamber 222. To this end, by locating, in one embodiment, the radial slots 162 along an interior side of the respective tube 42a, 42b and in highly close proximity to the lumens 242a, 242b that otherwise are in direct fluid communication with the patient's nares, the pressure monitoring circuit is able to detect a pressure nearly identical to that actually being seen by the patient (within 0.2-0.3 cm of actual pressure delivered to patient).

Notably, the nCPAP device 22, and in particular the generator body 30, in accordance with principles of the present disclosure is useful with a wide variety of other patient interface piece configurations that may or may not incorporate some or all of the features described above with respect to the patient interface piece 32. Thus, the patient interface piece 32 is in no way limiting.

Figure 10A:
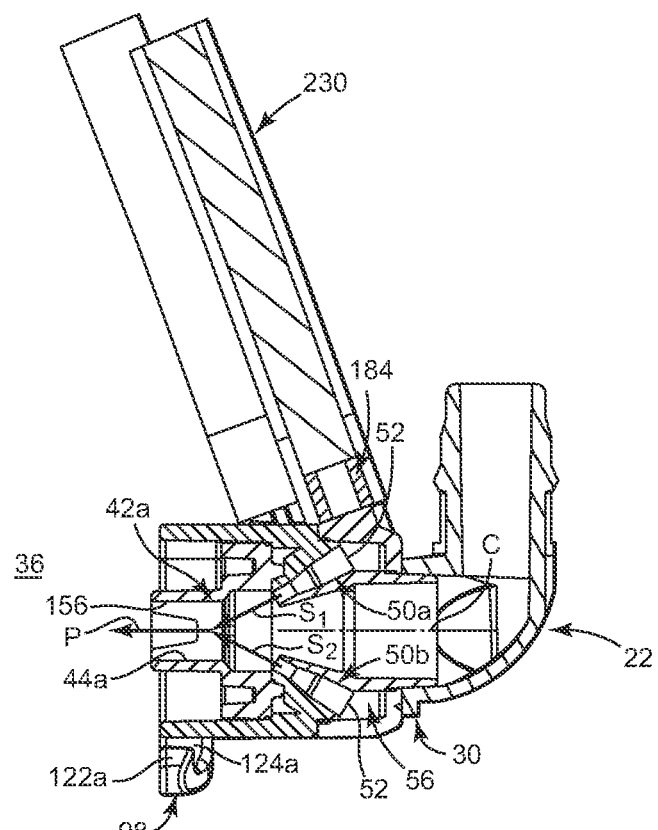
FIG. 10A is a cross-sectional view of the nCPAP device of FIG. 8C illustrating fluid flow during an inspiratory phase of operation.

Operation of the nCPAP device 22, and in particular the generator body 30, as part of the nCPAP system 20 (FIG. 1) is described with initial reference to FIG. 10A. For ease of illustration, the nCPAP device 22 is shown without the patient interface piece 32 (FIG. 9A). With this in mind, the nCPAP device 22 is secured to a patient (not shown). While the nCPAP device 22 of the present disclosure is useful with a wide variety of patients, the nCPAP device 22 is highly appropriate for providing CPAP therapy to infants or neonates. Regardless, the nCPAP device 22 is mounted to the patient by securing a strap (not shown) about the patient's head, and then securing the strap to the mounting features 98 provided by the generator body 30. For example, the strap(s) is secured to the generator body 30 by nesting the strap(s) within the gaps 124a, 124b (one of which is shown in FIG. 10A), with a positioning of the generator body 30 relative to the strap(s) being maintained by the clip 122a, 122b (one of which is shown in FIG. 10A).

Once secured to the patient, fluid (e.g., air, oxygen, etc.) is supplied to the generator body 30 via the supply tube 230. More particularly, fluid is forced into the supply port 184 that in turn directs the fluid flow into the manifold 56. The manifold 56 provides a fluid connection to the inlet end 52 of each of the nozzles 50 (designated generally; shown in FIG. 10A as the nozzles 50a, 50b), such that the supplied fluid is forced into the nozzles 50. The nozzles 50, in turn, each create a low momentum secondary jetstream fluid flow within the corresponding passageway 44a, 44b (FIG. 2A). For example, FIG. 10A illustrates the passageway 44a defined by the tube 42a, Along with the nozzles 50a, 50b. The first nozzle 50a creates a first, low momentum, secondary jetstream S1 within the passageway 44a. Similarly, the second nozzle 50b creates a second, low momentum, secondary jetstream S2 within the passageway 44a. As used throughout the specification, the phrase "low momentum" is in comparison to the nozzle-induced, jetstream momentum found with conventional nCPAP generators otherwise incorporating a single nozzle. By way of example, to deliver a CPAP of 5 cm of water, a single nozzle will be required to generate a jetstream momentum of 10 millinewton over a 0.2 inch diameter conduit. In contrast, with the generator body 30 embodiment shown, the CPAP of 5 cm of water is created with each of the nozzles 50a, 50b generating a jetstream momentum of 5 millinewton.

With additional reference to FIG. 4C, the first secondary jetstream S1 projects from the first nozzle 50a in the flow direction axis D1, whereas the second secondary jetstream S2 projects in the flow direction axis D2. Due to the previously described orientation of the nozzles 50a, 50b relative to the axial centerline C of the passageway 44a, the secondary jetstreams S1, S2 intersect and impinge upon one another approximately at the axial centerline C, creating a primary jetstream or jet pump P. Effectively, then, the low momentum secondary jetstreams S1, S2 combine with one another to establish or generate a stable, higher momentum jet pump flowing in a direction toward the patient (i.e., the patient side 36 of the generator body 30). The jet pump thus serves as a low momentum positive airway pressure source for the patient (i.e., momentum of the jet pump is converted into pressure).

During periods of time in which the patient is inhaling ("inspiratory phase"), the primary jetstream P readily flows toward the patient's nasal airways via the passageway 44a (and 44b). Because the interface point between the secondary jetstreams S1, S2 is at or about the reduced diameter proximal region 156 of the passageway 44a, any vortices (i.e., swirling fluid flow) produced by the impinging jetstreams S1, S2 are nominal and readily constrained within the passageway 44a. Thus, during the inspiratory phase, a continuous positive airway pressure is generated within, and delivered to the patient by, the passageways 44a, 44b. Further, by approximately centering the primary jetstream P within the respective passageway 44a, 44b, and providing the reduced diameter proximal region 156, a venturi effect is created that enhances entrainment of supplemental gas into the airflow toward the patient so as to meet the patient's inspiratory demands. In other embodiments, the generator body 30 is configured such that a diameter of at least one of the nozzles 50a, 50b can be varied. For example, a mandrel or pin can be slidably disposed within the nozzle 50a or 50b, and assembled thereto such that a user can move the pin toward or away from the outlet end 54, thus changing an effective diameter of the outlet end 54. This, in turn, allows the user to change the flow rate versus CPAP relationship to better meet the patient's work of breathing requirements.

Figure 10B:
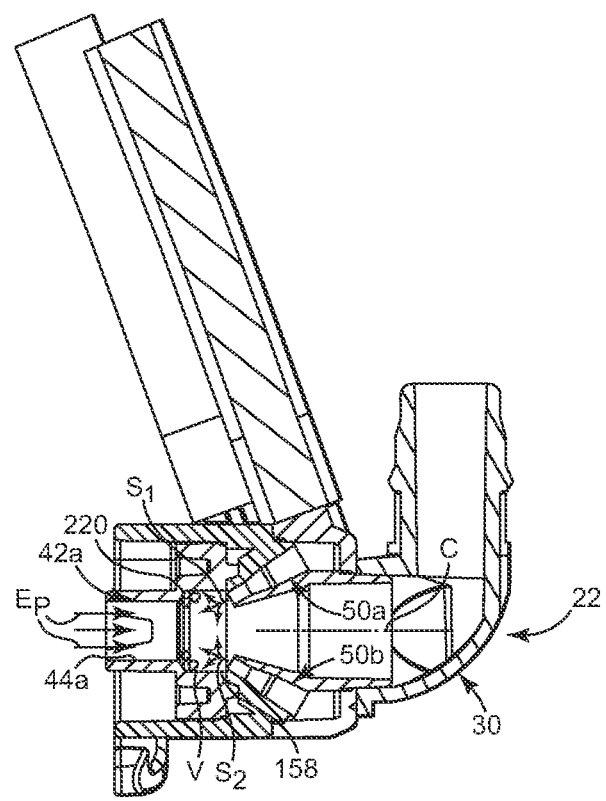
FIGS. 10B and 10C are cross-sectional views of the nCPAP device of FIG. 10A illustrating fluid flow during an expiratory phase of operation.
Figure 10C:
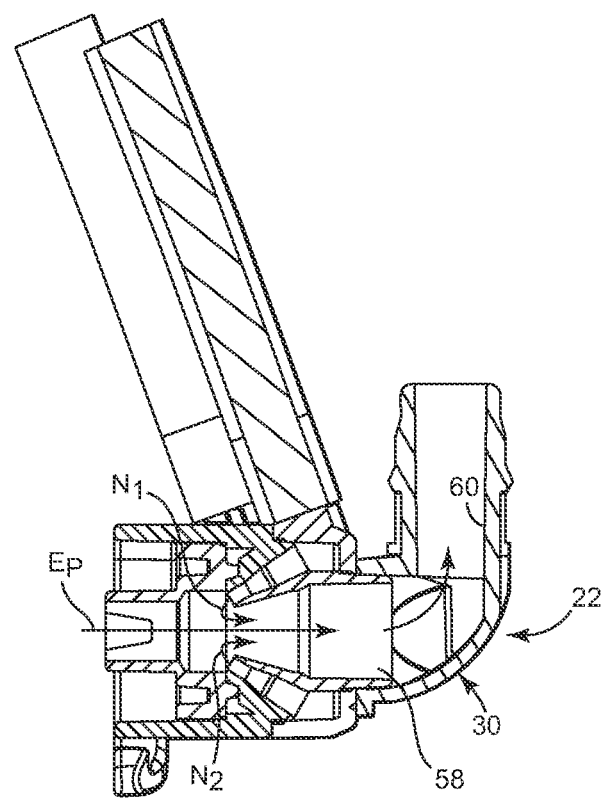

Operation of the nCPAP device 22 during periods of time in which the patient (not shown) exhales ("expiratory phase") is shown in FIG. 10B. As a point of reference, the flow rate of fluid being delivered to the generator body 30 is constant and thus does not change in either of the inspiratory phase or expiratory phase. Thus, pursuant to the previous discussion, the first and second secondary jetstreams S1, S2 continue to be produced by the nozzles 50a, 50b, respectively, and are directed into the corresponding passageway 44a, approaching the axial centerline C. However, during the expiratory phase, air exhaled by the patient enters the passageway 44a, flowing in the direction shown by the arrows Ep in FIG. 10B. The exhaled airflow Ep essentially simultaneously interacts with, or disrupts, the primary jetstream P (FIG. 10A), as well as the secondary jetstreams S1, S2. Disruption of the secondary jetstreams S1, S2 results in the secondary jetstreams S1, S2 no longer combining to form the primary jetstream P. Because the secondary jetstreams S1, S2 are low momentum and collectively provide a larger surface area (as compared to a single, high momentum jetstream), the exhaled air Ep readily achieves the desired jetstream disruption. As shown in FIG. 10B, the disrupted secondary jetstreams S1, S2 are caused to split and present minimal resistance to flow of the exhaled air Ep. Subsequently, the secondary jetstreams S1, S2 fold "back" with the exhaled airflow Ep. As a result, and as shown in FIG. 10C, the exhaled air Ep, as well as the "diverted" nozzle airflow N1, N2 readily flows through the passageway 44a, through the chamber 58 and the conduit 60, and is exhausted from the generator body 30 via the exhaust tubing 34. Fluid flow during the expiratory phase is shown by arrows in FIG. 10C.

The disruption in airflow may be characterized by the secondary jetstreams S1, S2 translating into or forming fairly large streamwise vortices (shown schematically in FIG. 10B for the secondary jetstreams S1, S2 at reference "V"). In alternative embodiments alluded to above, formation of streamwise vortices can be further induced by locating/orienting the nozzles 50a, 50b such that the secondary jetstreams S1, S2 impinge upon one another at a point displaced from the axial centerline C. In any event, the generated vortices V disperse away from the axial centerline C and into the relief zone 220 As a result, the streamwise vortices V prevent (or do not cause) occurrences of flow separation in the exhaled airflow. The above-described bend (or "flip") in flow direction from the nozzles 50a, 50b may be enhanced due to a coanda effect induced by the relief zone 220 wall. Regardless, resistance to the exhaled air Ep by the primary jetstream P and the secondary jetstreams S1, S2 is minimized along the relief zone 220, thus effectively increasing the hydraulic diameter of the exhaled air Ep flow path.

Figure 11A:
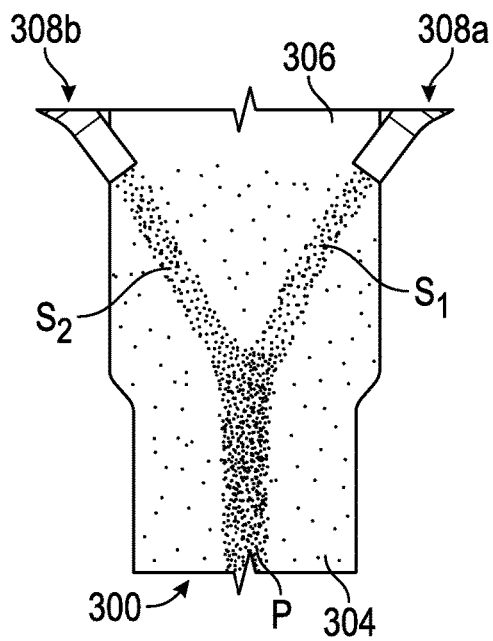
FIGS. 11A and 11B are photographs of a portion of an nCPAP device in accordance with the present disclosure during an inspiratory phase of operation.

The impinging jetstream and jetstream disruption features of the generator body 30 are reflected in the photographs of FIGS. 11A-12B. In particular, FIGS. 11A and 12A are longitudinal, cross-sectional views of fluid flow within a portion of a fluid circuit established by the generator body in accordance with principles of the present disclosure. By way of reference, the photographs of FIGS. 11A and 12A show a portion of a tube 300 (akin to the tube 42a or 42b of FIG. 2A) forming a passageway (akin to the passageway 44a or 44b of FIG. 2A) extending from a proximal side 304 to a distal side 306. Further, a pair of nozzles 308a, 308b (akin to the nozzles 50a, 50b of FIG. 2A) are fluidly connected to the passageway, and each generate a secondary, low momentum jetstream S1, S2 (referenced generally) within the tube 300.

Figure 11B:
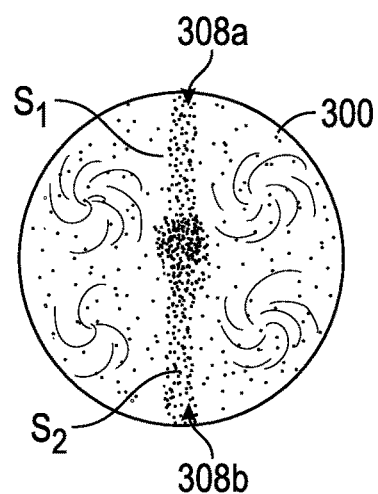

With the above in mind, FIG. 11A illustrates the inspiratory phase of operation, whereby the secondary jetstreams S1, S2 impinge upon one another within the tube 300, combining to produce a primary jetstream P. As previously described, the primary jetstream P is directed toward the proximal side 304 (and thus toward the patient (not shown)), and its momentum converts to positive pressure. As shown in FIG. 11B that otherwise provides a transverse cross-sectional photograph of airflow within the tube 300 adjacent the nozzles 308a, 308b during the inspiratory phase, the secondary jetstreams S1, S2 may generate airflow vortices V; however, these vortices V are relatively nominal or insubstantial, and do not otherwise extend to or interface with an inner surface of the tube 300.

Figure 12A:
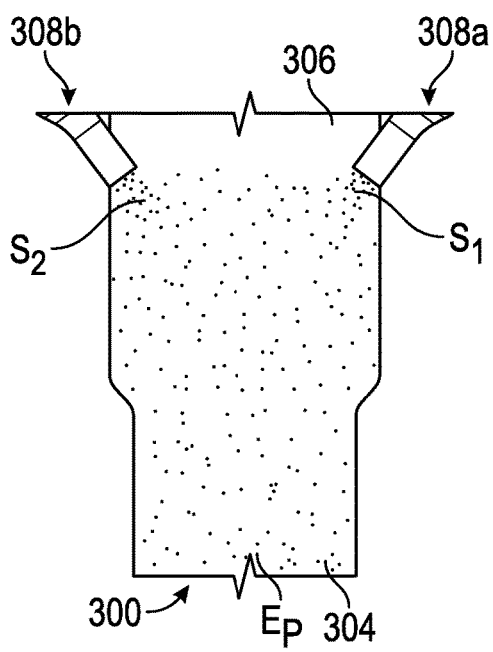
FIGS. 12A and 12B are photographs of the nCPAP device of FIGS. 11A and 11B during an expiratory phase of operation.
Figure 12B:
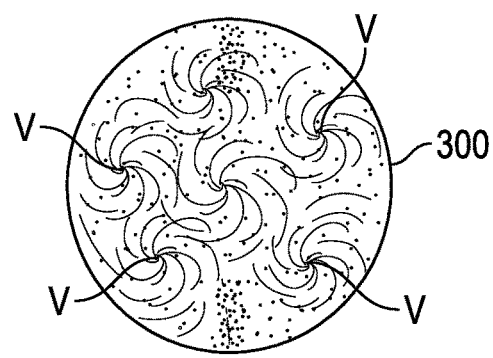

Conversely, during the expiratory phase, and as shown in FIG. 12A, exhaled air from the patient (referenced generally at Ep) readily disrupts the low momentum, secondary jetstreams S1, S2. Notably, the primary jetstream P (FIG. 11A) does not appear in FIG. 12A as the disruption of the secondary jetstreams S1, S2 prevents the secondary jetstreams S1, S2 from combining into the single, coherent primary jetstream P. FIG. 12B depicts the streamwise vortices V (swirling flow) generated secondary jetstreams S1, S2. The streamwise vortices V expand or disperse within the tube 300.

Notably, the low momentum jetstream fluid flow created by the nozzles 308 is easily disrupted by low momentum/pressure air exhaled from the patient. Thus, in marked contrast with previous nCPAP devices incorporating a single jetstream in conjunction with a fluidic flip technique during patient exhalation, the nCPAP device, and in particular the generator body, in accordance with principles of the present disclosure is characterized as requiring a reduced work of breathing by the patient. This is of great importance for patients with decreased lung capacity, such as infants or neonates. Further, by combining multiple nozzles/jetstreams within a single passageway, an outlet diameter of the nozzles can be reduced, as can overall size of the device. Because during normal operation the multiple nozzles are each generating low momentum jetstreams, audible noise produced by the nCPAP device of the present disclosure is reduced as compared to conventional variable flow nCPAP generators otherwise relying on a single nozzle, higher momentum jetstream.

Although the present disclosure has been described with reference to preferred embodiments, workers skilled in the art will recognize that changes can be made in form and detail without departing from the spirit and scope of the present disclosure.

Although the present disclosure has been described with reference to preferred embodiments, workers skilled in the art will recognize that changes can be made in form and detail without departing from the spirit and scope of the present disclosure.

What is claimed is:

1. A nasal continuous positive airway pressure (nCPAP) device comprising:
    a body having a proximal end and a distal end, a chamber at the proximal end of the body, and a first passage extending from the chamber through the distal end of the body;
    a plurality of nozzles, each having an outlet end that projects into the first passage, between the chamber and the distal end of the body, the plurality of nozzles arranged to direct a fluid flow into the first passage such that the fluid flow from each nozzle impinges upon each other and combines to flow through the first passage toward the distal end of the body;
    wherein an opposing fluid flow through the first passage from the distal end toward the proximal end of the body redirects the fluid flow from each nozzle to flow toward the chamber.

2. The device of claim 1, wherein an exhaust port extends through the proximal end of the body and is fluidly coupled to the chamber.

3. The device of claim 1, wherein the plurality of nozzles are non-parallel relative to each other and relative to a centerline through the first passage.

4. The device of claim 3, wherein the plurality of nozzles are transversely aligned relative to the centerline through the first passage.

5. The device of claim 3, wherein a fluid flow entering the first passage through each nozzle impinges upon each other at a point displaced from the centerline through the first passage.

6. The device of claim 1, wherein the plurality of nozzles extend into the first passage from an inner surface of the first passage.

7. The device of claim 1, wherein the body comprises a common manifold, each nozzle comprising an inlet end fluidly coupled to the common manifold.

8. The device of claim 1, wherein a second passage extends from the chamber through the distal end of the body.

9. The device of claim 8, wherein a slot extends through a wall of the first passage and a wall of the second passage, proximal to the distal end of the body.

10. The device of claim 9, wherein the body comprises a pressure monitoring port fluidly connected to the radial slot of the first passage and the second passage.

11. A nasal continuous positive airway pressure (nCPAP) device comprising:
    a body having a proximal end and a distal end, a chamber at the proximal end of the body, and a first passage extending from the chamber through the distal end of the body;
    a plurality of nozzles, each having an outlet end that projects from an inner surface of the first passage into the first passage, between the chamber and the distal end of the body;
    wherein each outlet end is oriented to direct a fluid flow from the nozzle into the first passage such that the fluid flow from each nozzle impinges upon each other and combines to flow through the first passage toward the distal end of the body and wherein an opposing fluid flow through the first passage from the distal end toward the proximal end of the body redirects the fluid flow from each nozzle to flow toward the chamber.

12. The device of claim 11, wherein an exhaust port extends through the proximal end of the body and is fluidly coupled to the chamber.

13. The device of claim 11, wherein the plurality of nozzles are non-parallel relative to each other and relative to a centerline through the first passage.

14. The device of claim 13, wherein the plurality of nozzles are transversely aligned relative to the centerline through the first passage.

15. The device of claim 13, wherein a fluid flow entering the first passage through each nozzle impinges upon each other at a point displaced from the centerline through the first passage.

16. The device of claim 11, wherein the body comprises a common manifold, each nozzle comprising an inlet end fluidly coupled to the common manifold.

17. The device of claim 11, wherein a second passage extends from the chamber through the distal end of the body.

18. The device of claim 17, wherein a slot extends through a wall of the first passage and a wall of the second passage, proximal to the distal end of the body.

19. The device of claim 18, wherein the body comprises a pressure monitoring port fluidly connected to the radial slot of the first passage and the second passage.

20. The device of claim 11, wherein each nozzle comprises a cavity with an inner surface having a cross-sectional width that tapers from an inlet end toward the outlet end.

* * * * *